United States Patent [19]

Terada et al.

[11] 4,448,915
[45] May 15, 1984

[54] ACETYLENE CARBAMIDE DERIVATIVES, PROCESSES FOR THEIR PRODUCTION, AND ANTIOXIDANTS FOR ORGANIC SUBSTANCES WHICH COMPRISE SUCH DERIVATIVES AS ACTIVE INGREDIENTS

[75] Inventors: Yutaka Terada, Nishinomiya; Yukoh Takahashi; Shinichi Yachigo, both of Toyonaka; Tamaki Ishii, Suita, all of Japan

[73] Assignee: Sumitomo Chemical Co., Ltd., Osaka, Japan

[21] Appl. No.: 435,187

[22] Filed: Oct. 19, 1982

[30] Foreign Application Priority Data

Oct. 19, 1981 [JP] Japan ................. 56-167434

[51] Int. Cl.³ .................. C07D 515/08; C08K 5/34
[52] U.S. Cl. ........................ 524/93; 548/304
[58] Field of Search ................ 524/93; 548/304

[56] References Cited

U.S. PATENT DOCUMENTS 3,008,936 11/1961 Kamlet ........................ 524/93
3,531,483 9/1970 Gilles ......................... 524/101
3,909,491 9/1975 Gilles ......................... 524/101
4,339,383 7/1982 Wehner et al. ................ 548/304

FOREIGN PATENT DOCUMENTS 2010875A 7/1979 United Kingdom .

Primary Examiner—Veronica P. Hoke
Attorney, Agent, or Firm—Sughrue, Mion, Zinn, Macpeak & Seas

[57] ABSTRACT

An acetylene carbamide derivative of the general formula (I):

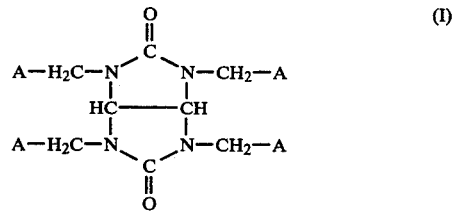

wherein A represents

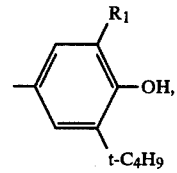

wherein $R_1$ represents a hydrogen atom or an alkyl group having 1 to 4 carbon atoms, is disclosed. A process for producing the acetylene carbamide derivative of the general formula (I) is also disclosed. The acetylene carbamide derivative of the invention is useful as a stabilizer for organic substances from heat and oxidation.

22 Claims, No Drawings

ACETYLENE CARBAMIDE DERIVATIVES, PROCESSES FOR THEIR PRODUCTION, AND ANTIOXIDANTS FOR ORGANIC SUBSTANCES WHICH COMPRISE SUCH DERIVATIVES AS ACTIVE INGREDIENTS

FIELD OF THE INVENTION

The present invention relates to acetylene carbamide derivatives of the general formula (I):

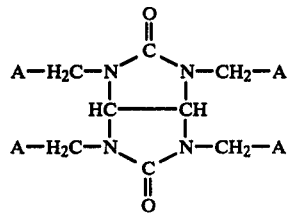

wherein A represents

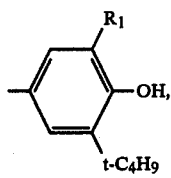

in which $R_1$ represents a hydrogen atom or an alkyl group having 1 to 4 carbon atoms; processes for their production; and antioxidants for polymers which contain such derivatives as active ingredients.

BACKGROUND OF THE INVENTION

Synthetic resins such as polyolefins, acrylonitrile-butadiene-styrene copolymers (ABS resins), polystyrene, high impact polystyrene, polyamides, polyacetals, ethylene-propylene copolymers, etc.; natural rubbers; synthetic rubbers such as butadiene rubber, isoprene rubber, isoprene-isobutylene copolymer rubbers, styrene-butadiene copolymer rubbers, acrylonitrile-butadiene copolymer rubbers, ethylene-propylene-diene terpolymers (EPDM), etc.; petroleum products such as lubricants, fuel oils, etc.; and various other organic substances such as fats and oils, greases, etc., are susceptible to deterioration by light or oxygen. Hence, in order to inhibit such deterioration, various deterioration inhibiting agents such as, for example, phenolic compounds, e.g., 2,6-di-t-butyl-4-methylphenol, n-octadecyl 3-(3,5-di-t-butyl-4-hydroxyphenyl)propionate, tetrakis[3-(3,5-di-t-butyl-4-hydroxyphenyl)propionyloxymethyl]methane, etc., have hitherto been employed. However, any of these agents has a disadvantge that when incorporated in an organic substance at a high temperature for a prolonged period, it lacks the duration of the effect.

Under such circumstances, the present inventors have been intensively studying for the purpose of developing an excellent antioxidant which can improve such disadvantage, and have discovered that acetylene carbamide derivatives having a specific structure represented by the above general formula (I) exhibit an excellent effect, thus having accomplished the present invention.

SUMMARY OF THE INVENTION

An object of the present invention is to provide an acetylene carbamide derivative of the general formula (I):

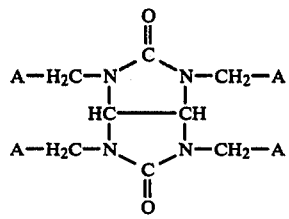

wherein A represents

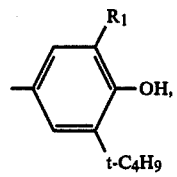

in which $R_1$ represents a hydrogen atom or an alkyl group having 1 to 4 carbon atoms.

Another object of the present invention is to provide a process for producing the acetylene carbamide derivative of the general formula (I).

A further object of the present invention is to provide a stabilizer for organic substances containing the acetylene carbamide derivative of the general formula (I).

DETAILED DESCRIPTION OF THE INVENTION

The acetylene carbamide derivatives of the above general formula (I) are novel compounds which have been synthesized by the present inventors for the first time and hence have not been described in any literature and which can be produced from as a starting material acetylene carbamide of the general formula (II):

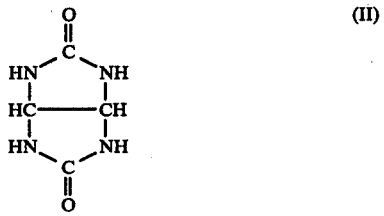

by the following processes:

(A) A process which comprises reacting acetylene carbamide and a p-hydroxybenzyl alcohol derivative of the general formula (III):

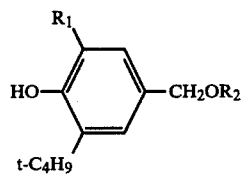

wherein R₁ is as defined above, and R₂ represents a hydrogen atom or an alkyl group having 1 to 4 carbon atoms, in a solvent in the presence of a catalyst.

(B) A process which comprises reacting acetylene carbamide and a dialkyldithiocarbamate derivative of the general formula (IV):

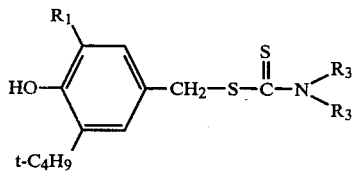

(IV)

wherein R₁ is as defined above, and R₃ represents an alkyl group having 1 to 4 carbon atoms, in a solvent in the presence of a catalyst.

(C) A process which comprises simultaneously reacting acetylene carbamide, formaldehyde and a phenol of the general formula (V):

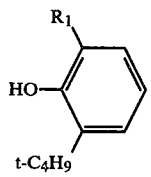

(V)

wherein R₁ is as defined above, in a solvent in the presence of a catalyst.

In the starting compounds used in the abovedescribed respective processes, examples of the p-hydroxybenzyl alcohol derivative of the general formula (III) include 3-t-butyl-4-hydroxybenzyl alcohol, 3-methyl-5-t-butyl-4-hydroxybenzyl alcohol, 3,5-di-t-butyl-4-hydroxybenzyl alcohol, 3-propyl-5-t-butyl-4-hydroxybenzyl alcohol, 3-t--butyl-4-hydroxybenzyl methyl ether, 3-methyl-5-t-butyl-4-hydroxybenzyl methyl ether, 3,5-di-t-butyl-4-hydroxybenzyl methyl ether, 3,5-di-t-butyl-4-hydroxybenzyl butyl ether, etc.; examples of the dialkyldithiocarbamate derivative of the general formula (IV) include 3-t-butyl-4-hydroxybenzyl-N,N-dimethyldithiocarbamate, 3-methyl-5-t-butyl-4-hydroxybenzyl-N,N-diethyldithiocarbamate, 3,5-di-t-butyl-4-hydroxybenzyl-N,N-dimethyldithiocarbamate, etc.; and examples of the phenol of the general formula (V) include 2-t-butylphenol, 2-methyl-6-t-butylphenol, 2,6-di-t-butylphenol, etc.

In each reaction of the above processes (A) to (C), the molar ratio of the respective reactants is as follows:

In the process (A), the molar ratio of the p-hydroxybenzyl alcohol derivative to acetylene carbamide is generally 3.5:1 to 6:1, preferably 4:1 to 5:1, more preferably 4.2:1 to 4.6:1.

In the process (B), the molar ratio of the dialkyldithiocarbamate derivative to acetylene carbamide is generally 3.5:1 to 5:1, preferably 4:1 to 4.6:1.

In the process (C), the molar ratio of acetylene carbamide to the phenol to formaldehyde is generally 1:3.5 to 8:3.5 to 8, preferably 1:4 to 6:4 to 6.

In each reaction of the above processes (A) to (C), there can be employed as the solvent lower alcohols such as methanol, ethanol, n-propyl alcohol, isopropyl alcohol, n-butyl alcohol, isobutyl alcohol, sec-butyl alcohol, etc., with methanol and ethanol being preferable. Further, in combination with these alcohols, it is also possible to use other organic solvents such as aliphatic hydrocarbons, e.g., n-hexane, n-heptane, etc.; alicyclic hydrocarbons, e.g., cyclohexane, etc.; aromatic hydrocarbons, e.g., benzene, toluene, xylene, etc.; halogenated hydrocarbons, e.g., chloroform, carbon tetrachloride, etc.; aprotonic polar solvents, e.g., N,N-dimethylformamide, dimethyl sulfoxide, etc.; and the like.

While the reaction temperature varies depending on the kind of solvent used, it is generally about 20° C. to about 200° C., preferably 40° to 150° C. The reaction, however, is generally carried out at the reflux temperature.

Examples of the catalyst which can be used include a basic catalyst such as an alkali metal hydroxide, e.g., lithium hydroxide, sodium hydroxide, potassium hydroxide, etc.; an alkali metal alkoxide, e.g., sodium methoxide, potassium methoxide, sodium ethoxide, potassium ethoxide, potassium t-butoxide, etc.; and the like.

A suitable amount of the catalyst which can be used is generally 0.1 to 6 moles, preferably 4 to 5 moles, in the process (A); generally 3.5 to 12 moles, preferably 8 to 10 moles, in the process (B); and generally 0.1 to 9 moles, preferably 4 to 6 moles, in the process (C), per mole of acetylene carbamide, respectively.

Separation of the desired product from each reaction mixture obtained by the processes (A) to (C) can be achieved by a conventional method, e.g., (1) a method in which if desired, an acid is added to the reaction mixture to neutralize the catalyst, the solvent is distilled off, a solvent which is insoluble or sparingly soluble in water but which can dissolve therein the desired product, such as toluene, ethyl acetate, etc., is added to the concentrate to thereby extract the desired product, and the extract is washed with water and then concentrated, or (2) a method in which the basic catalyst present in the reaction mixture is neutralized, and precipitated crystals are separated by filtration with or without the solvent having been removed. The thus separated desired product can be purified by a conventional method such as further recrystallization or solvent-washing.

Typicals of the acetylene carbamide derivative of the general formula (I) thus obtained in the present invention are listed below:

N,N',N'',N'''-Tetrakis(3-t-butyl-4-hydroxybenzyl)acetylene carbamide

N,N',N'',N'''-Tetrakis(3-methyl-5-t-butyl-4-hydroxybenzyl)acetylene Carbamide

N,N',N'',N'''-Tetrakis(3-ethyl-5-t-butyl-4-hydroxybenzyl)acetylene Carbamide

N,N',N'',N'''-Tetrakis(3-n-propyl-5-t-butyl-4-hydroxybenzyl)acetylene Carbamide

N,N',N'',N'''-Tetrakis(3,5-di-t-butyl-4-hydroxybenzyl)acetylene Carbamide

These acetylene carbamide derivatives are effective as antioxidants for synthetic resins such as polyolefins, acrylonitrile-butadiene-styrene copolymers (ABS resins), polystyrene, high impact polystyrene, polyamides, polyacetals, ethylene-propylene copolymers, etc.; natural rubbers; synthetic rubbers such as butadiene rubber, isoprene rubber, styrene-butadiene copolymer rubbers, acrylonitrile-butadiene rubbers, EPDM, etc.; petroleum products such as lubricants, fuel oils, etc.; and various other organic substances. Particularly, the acetylene carbamide derivatives of the present invention are effective against the oxidative deterioration of polyolefin resins, styrenic resins and synthetic rubbers produced by the solution polymerization process, and inter alia, polypropylene resin, ABS resins and butadiene rubber are most effectively protected.

When the acetylene carbamide derivatives of this invention are used as antioxidants, the amount to be used varies depending on the kind of organic substance to be stabilized, but it is generally about 0.001 to about 10% by weight based on the weight of the organic substance, and in many applications, it is about 0.01 to about 5% by weight based on the amount of the organic substance.

For incorporating the acetylene carbamide derivative of this invention in an organic substance, conventional known equipments and methods can be employed.

While the acetylene carbamide derivatives of this invention are effective as antioxidants for organic substances even when used alone, an excellent synergistic effect can be obtained when they are used in combination with a sulfur-based antioxidant such as a dialkyl-3,3'-thiodipropionate of the general formula (VI):

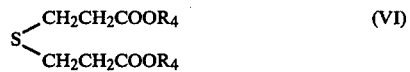

(VI)

wherein $R_4$ is an alkyl group having 12 to 20 carbon atoms, e.g., dilauryl-3,3'-thiodipropionate, dimyristyl-3,3'-thiodipropionate, distearyl-3,3'-thiodipropionate, etc.; a pentaerythritol-tetrakis($\beta$-alkylthiopropionate) of the general formula (VII):

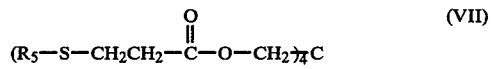

(VII)

wherein $R_5$ is an alkyl group having 4 to 20, preferably 12 to 20, carbon atoms, e.g., pentaerythritol-tetrakis-($\beta$-laurylthiopropionate), pentaerythritol-tetrakis($\beta$-stearylthiopropionate), etc.; distearyl disulfide; and the like.

When the sulfur-based antioxidant is used in combination, the amount thereof is generally 0.5 to 15 times the weight of the acetylene carbamide derivative of this invention, and the total amount of the acetylene carbamide derivative and the sulfur-based antioxidant is preferably 0.01 to 10 parts by weight per 100 parts by weight of the organic substance.

Furthermore, the light resistance can be improved by incorporating thereinto an ultraviolet absorber, an organonickel light stabilizer, a hindered amine light stabilizer and the like, such as 2-(2-hydroxy-4-octoxyphenyl)benzotriazole, 2-(2-hydroxy-5-methylphenyl)benzotriazole, 2-(2-hydroxy-3,5-di-t-butylphenyl)-5-chlorobenzotriazole, 2-(2-hydroxy-3,5-di-t-butylphenyl)benzotriazole, 2-(2-hydroxy-3-t-butyl-5-methylphenyl)-5-chlorobenzotriazole, 2-(2-hydroxy-3-t-butyl-5-methylphenyl)benzotriazole, 2-(2-hydroxy-3,5-di-t-amylphenyl)-5-chlorobenzotriazole, 2-(2-hydroxy-3,5-di-t-amylphenyl)benzotriazole, 2-(2-hydroxy-5-t-octylphenyl)benzotriazole, 2,4-dihydroxybenzophenone, 2-hydroxy-4-methoxybenzophenone, 2-hydroxy-4-octoxybenzophenone, 2-hydroxy-4-dodecyloxybenzophenone, 2-hydroxy-4-benzyloxybenzophenone, 2,4,2',4'-tetrahydroxybenzophenone, 2,2'-dihydroxy-4,4'-dimethoxybenzophenone, [2,2'-thiobis(4-t-octylphenolato)]-n-butylamine nickel (II), [2,2'-thiobis(4-t-octylphenolato)]triethanolamine nickel (II), [2,2'-thiobis(4-t-octylphenolato)]cyclohexyldiethanolamine nickel (II), bis(3,5-di-t-butyl-4-hydroxylbenzylphosphoric acid) monoethyl ester nickel salt, bis(2,2,6,6-tetramethyl-4-piperidyl)sebacate, 4-benzoyloxy-2,2,6,6-tetramethylpiperidine, bis(2,2,6,6-tetramethyl-4-piperidinyl)-para-phenylenediacetate, bis(1,2,2,6,6-pentamethylpiperidin-4-yl) 2-(3,5-di-t-butyl-4-hydroxybenzyl)-2-n-butyl malonate, 1-{2-[3-(3,5-di-t-butyl-4-hydroxyphenyl)propionyloxy]ethyl}-4-[3-(3,5-di-t-butyl-4-hydroxyphenyl)propionyloxy]-2,2,6,6-tetramethylpiperidine, dimethyl succinate-1-(2-hydroxyethyl)-4-hydroxy-2,2,6,6-tetramethylpiperidine polycondensate, 1,4-bis(2,2,6,6-tetramethylpiperidin-4-carbonyloxymethyl)-cyclohexane, etc.

Still further, the color hue can be enhanced by incorporating a phosphorus-based antioxidant such as tris(mono- and/or di-nonylphenyl) phosphite, tris(2,4-di-t-butylphenyl) phosphite, tris(2-t-butyl-4-methylphenyl) phosphite, tetrakis(2,4-di-t-butylphenyl)-4,4'-biphenylene phosphite, 3,9-bis(octadecyloxy)-2,4,8,10-tetraoxa-3,9-diphosphorspyro[5,5]undecane, 3,9-bis(dodecyloxy)-2,4,8,10-tetraoxa-3,9-diphosphorspyro[5,5]undecane, 3,9-bis(octoxy)-2,4,8,10-tetraoxa-3,9-diphosphorspyro[5,5]undecane, tetrakis(2,4-di-t-butylphenyl) [1,1'-biphenyl]-4,4'-diylbisphosphonite, etc.

In addition to the above, other antioxidants and light stabilizers, as well as plasticizers, nucleating agents, lubricating agents, antistatic agents, flame retardants, metal inactivating agents, metal soaps, pigments and dyes, fillers, anticorrosives, rust preventives, pour point depressants, defoaming agents, dispersants, extreme pressure additives, etc., can be incorporated depending upon the respective purposes, if desired.

When such various additives are employed in combination, they can be mixed with the acetylene carbamide derivative of the present invention in advance, and there is no specific limitation in the combination use thereof.

The present invention is more particularly described by the following examples.

EXAMPLE 1

Into a 300 ml four-necked flask equipped with a thermometer, a stirrer and a condenser were charged 40.36 g (0.138 mole) of 3,5-di-t-butyl-4-hydroxybenzyl butyl ether, 4.26 g (0.03 mole) of acetylene carbamide and 50 ml of butanol. After purging the flask with nitrogen, 8.60 g (0.138 mole) of 85 wt% potassium hydroxide was added thereto, the temperature was elevated, and the reaction was carried out under reflux condition for 3 hours. After completion of the reaction, the reaction mixture was treated with 75 ml (0.15 mole) of 2 N hydrochloric acid and then extracted with 100 ml of toluene. The extracted toluene layer was washed with water and then concentrated under reduced pressure, and 50 ml of n-hexane was added to the concentrate to thereby subject to recrystallization to obtain 28.94 g (yield: 95%) of N,N',N'',N'''-tetrakis(3,5-di-t-butyl-4-hydroxybenzyl)acetylene carbamide as white crystals having a melting point of 244° to 246° C.

Elemental analysis for $C_{64}H_{94}N_4O_6$ (calculated values in parentheses): C: 75.30%, (75.70%); H: 9.45%, (9.33%); N: 5.46%, (5.52%).

FD-MS: Molecular ion peak: 1014.

$^1$H-NMR (CDCl$_3$, TMS): $\delta$1.37, 72H, s; $\delta$4.10, 4H, d, J=15 Hz; $\delta$4.57, 4H, d, J=15 Hz; $\delta$4.96, 2H, s; $\delta$5.14, 4H, s; $\delta$6.97 8H, s.

EXAMPLE 2

Into a 200 ml four-necked flask equipped with a thermometer, a stirrer and a condenser were charged 9.57 g (0.046 mole) of 3-t-butyl-5-methyl-4-hydroxybenzyl methyl ether, 1.42 g (0.010 mole) of acetylene carbamide and 20 ml of methanol. After purging the flask with nitrogen, 8.87 g (0.046 mole) of a 28 wt% solution of sodium methoxide in methanol was added thereto, the temperature was elevated, and the reaction was carried out under reflux condition for 40 hours. After completion of the reaction, the reaction mixture was treated with 30 ml (0.06 mole) of 2 N hydrochloric acid, and then extracted with 100 ml of ethyl acetate. The extracted ethyl acetate layer was treated in the same manner as in Example 1 to obtain 7.87 g (yield: 93%) of N,N',N'',N'''-tetrakis(3-t-butyl-5-methyl-4-hydroxybenzyl)acetylene carbamide as white crystals having a melting point of 225° to 227° C.

Elemental analysis for $C_{52}H_{70}N_4O_6$ (calculated values in parentheses): C: 73.91%, (73.77%); H: 8.35%, (8.28%); N: 6.58%, (6.62%).

FD-MS: Molecular ion peak: 846.

$^1$H-NMR (CDCl$_3$, TMS): $\delta$1.33, 36H, s; $\delta$2.13, 12H, s; $\delta$3.97, 4H, d, J=15 Hz; $\delta$4.80, 4H, s; $\delta$4.81, 4H, d, J=15 Hz; $\delta$4.87, 2H, s; $\delta$6.64; 4H, br. s; $\delta$6.93, 4H, br. s.

EXAMPLE 3

N,N',N'',N'''-tetrakis(3-t-butyl-4-hydroxybenzyl)acetylene carbamide can be obtained by repeating the same procedure as in Example 2 from 3-t-butyl-4-hydroxybenzyl alcohol and acetylene carbamide with a 28 wt% solution of sodium methoxide in methanol as a catalyst being used, respectively.

EXAMPLE 4

Into the same reactor as used in Example 1 were charged 15.62 g (0.046 mole) of 3,5-di-t-butyl-4-hydroxybenzyldimethyldithiocarbamate, 1.42 g (0.01 mole) of acetylene carbamide and 50 ml of methanol. After purging the reactor was nitrogen, 6.59 g (0.10 mole) of 85 wt% potassium hydroxide was added thereto as a catalyst, and the reaction was carried out under reflux condition for 3 hours. After completion of the reaction, the reaction mixture was post-treated in the same manner as in Example 1 to separate and purify the product. Thus, 9.85 g (yield: 97%) of N,N',N'',N'''-tetrakis(3,5-di-t-butyl-4-hydroxybenzyl)acetylene carbamide was obtained as white crystals.

EXAMPLE 5

In the same manner as in Example 4, 14.97 g (0.046 mole) of 3-t-butyl-5-methyl-4-hydroxybenzyldiethyldithiocarbamate and 1.42 g (0.01 mole) of acetylene carbamide were reacted under reflux condition in a methanol solvent in the presence of 19.28 g (0.01 mole) of a 28 wt% solution of sodium methoxide in methanol as a catalyst for 10 hours, and then post-treated in the same manner as in Example 2 to obtain 7.79 g (yield: 92%) of N,N',N'',N'''-tetrakis(3-t-butyl-5-methyl-4-hydroxybenzyl)acetylene carbamide as white crystals.

EXAMPLE 6

Into the same reactor as used in Example 2 were charged 11.55 g (0.056 mole) of 2,6-di-t-butylphenol, 1.42 g (0.01 mole) of acetylene carbamide, 3.65 g (0.056 mole) of a 46 wt% solution of formaldehyde in methanol, 25 ml of methanol and 25 ml of n-hexane. After purging the reactor with nitrogen, 3.69 g (0.056 mole) of 85 wt% potassium hydroxide was added thereto, the temperature was elevated and the reaction was carried out under reflux condition for 10 hours. After completion of the reaction, the reaction mixture was treated with 30 ml (0.06 mole) of 2 N hydrochloric acid, and post-treated in the same manner as in Example 1 to obtain 9.75 g (yield: 96%) of N,N',N'',N'''-tetrakis(3,5-di-t-butyl-4-hydroxybenzyl)acetylene carbamide as white crystals.

EXAMPLE 7

The same procedure as in Example 6 was repeated except that the 2,6-di-t-butylphenol was replaced by 2-t-butyl-6-methylphenol. The product was isolated from the reaction mixture to obtain N,N',N'',N'''-tetrakis(3-t-butyl-5-methyl-4-hydroxybenzyl)acetylene carbamide.

EXAMPLE 8

Into a 200 ml four-necked flask equipped with a water separator, a thermometer and a stirrer were charged 6.24 g (0.027 mole) of 3,5-di-t-butyl-4-hydroxybenzyl alcohol, 0.84 g (0.006 mole) of acetylene carbamide and 50 g of toluene. After purging the reactor with nitrogen, 1.0 g (0.005 mole) of a 28 wt% solution of sodium methoxide in methanol was added thereto, and the reaction was carried out under reflux condition for 5 hours. After completion of the reaction, the reaction mixture was neutralized with 2.5 ml (0.005 mole) of 2 N hydrochloric acid, and post-treated in the same manner as in Example 1 to obtain 3.5 g (yield: 58%) of N,N',N'',N'''-tetrakis(3,5-di-t-butyl-4-hydroxybenzyl)acetylene carbamide as white crystals.

EXAMPLE 9

Into the same reactor as used in Example 8 were charged 5.8 g (0.03 mole) of 3-t-butyl-5-methyl-4-hydroxybenzyl alcohol, 0.84 g (0.006 mole) of acetylene carbamide and 30 g of p-xylene. After purging the reactor with nitrogen, 2.0 g (0.008 mole) of a 28 wt% solution of potassium methoxide in methanol was added thereto, and the reaction was carried out at 140° C. for 8 hours. After completion of the reaction, the reaction mixture was neutralized with 4 ml (0.008 mole) of 2 N hydrochloric acid, and post-treated in the same manner as in Example 2 to obtain 2.8 g (yield: 55%) of N,N',N'',N'''-tetrakis(3-t-butyl-5-methyl-4-hydroxybenzyl)acetylene carbamide as white crystals.

EXAMPLE 10

N,N',N'',N'''-tetrakis(3-t-butyl-4-hydroxybenzyl)acetylene carbamide can be obtained by repeating the same procedure as in Example 8 from 3-t-butyl-4-hydroxybenzyl alcohol and acetylene carbamide with toluene as a solvent and a 28 wt% solution of sodium methoxide in methanol as a catalyst being used, respectively.

EXAMPLE 11

Each following formulation was mixed in a mixer for 5 minutes, and melted and kneaded by means of a mixing roll at 180° C. to obtain a compound which was then molded into a sheet of 1 mm in thickness using a hot press at 210° C. Thus, a test piece of 40×40×1 mm was prepared. The time to when the test piece had become brittle to an extent of 30% of the surface area thereof was measured in a gear oven at 160° C., and this was designated as a thermal brittleness induction period.

Thus, stability against heat and oxidation was evaluated. The results obtained are given in Table 1.

| Formulation | |
|---|---|
| Non-stabilized Polypropylene Resin | 100 Parts by weight |
| Calcium Stearate | 1 Part by weight |
| Test Compound | As indicated in Table 1 |

The symbols under the test compounds in Table 1 stand for the following compounds, respectively.

| | |
|---|---|
| I-1 | N,N',N'',N'''—Tetrakis(3,5-di-t-butyl-4-hydroxybenzyl)acetylene Carbamide |
| I-2 | N,N',N'',N'''—Tetrakis(3-t-butyl-5-methyl-4-hydroxybenzyl)acetylene Carbamide |
| AO-1 | n-Octadecyl 3-(3,5-di-t-butyl-4-hydroxyphenyl)-propionate |
| AO-2 | 1,1,3-Tris(3-t-butyl-6-methyl-4-hydroxyphenyl)butane |
| AO-3 | Tetrakis[3-(3,5-di-t-butyl-4-hydroxyphenyl)-propionyloxymethyl]methane |
| AO-4 | Dimyristyl 3,3'-Thiodipropionate |
| AO-5 | Pentaerythritol-tetrakis(β-laurylthiopropionate) |

TABLE 1

| Test Compound | Present Invention Run No. | | | | | | | |
|---|---|---|---|---|---|---|---|---|
| | 1 | 2 | 3 | 4 | 5 | 6 | 7 | 8 |
| Phenol Type | | | | | | | | |
| I-1 | 0.05 | | 0.05 | 0.05 | | | | |
| I-2 | | 0.05 | | | 0.05 | 0.05 | 0.05 | 0.05 |
| AO-1 | | | | | | | | |
| AO-2 | | | | | | | | |
| AO-3 | | | | | | | | |
| Sulfur Type | | | | | | | | |
| AO-4 | | | 0.2 | | 0.2 | 0.4 | | |
| AO-5 | | | | 0.2 | | | 0.2 | 0.4 |
| Brittleness Induction Period (hrs) | 80 | 75 | 760 | 730 | 730 | 910 | 1470 | 2020 |

| Test Compound | Comparison Run No. | | | | | | | |
|---|---|---|---|---|---|---|---|---|
| | 9 | 10 | 11 | 12 | 13 | 14 | 15 | 16 |
| Phenol Type | | | | | | | | |
| I-1 | | | | | | | | |
| I-2 | | | | | | | | |
| AO-1 | 0.05 | | | 0.05 | 0.05 | | | |
| AO-2 | | 0.05 | | | | 0.05 | 0.05 | |
| AO-3 | | | 0.05 | | | | | 0.05 |
| Sulfur Type | | | | | | | | |
| AO-4 | | | | 0.2 | | 0.2 | | 0.2 |
| AO-5 | | | | | 0.2 | | 0.2 | |
| Brittleness Induction Period (hrs) | 30 | 25 | 50 | 320 | 310 | 380 | 390 | 490 |

| Test Compound | Comparison Run No. | | | |
|---|---|---|---|---|
| | 17 | 18 | 19 | 20 |
| Phenol Type | | | | |
| I-1 | | | | NO ADDITION |
| I-2 | | | | " |
| AO-1 | | | | " |
| AO-2 | | | | " |
| AO-3 | 0.05 | 0.05 | 0.05 | " |
| Sulfur Type | | | | |
| AO-4 | 0.4 | | | " |
| AO-5 | | 0.2 | 0.4 | " |
| Brittleness Induction | 610 | 400 | 550 | 5 |

EXAMPLE 12

100 parts by weight of a non-stabilized ABS resin powder was added to a grinder and dispersed in an appropriate amount of methanol. 0.5 part by weight of each test compound was added thereto, and the methanol was evaporated while intimately mixing the mixture. The thus obtained ABS resin powder was used as a test sample. Stability against heat and oxidation was evaluated in terms of degree of discoloration of the ABS resin powder after aging in a gear oven at 180° C. The results obtained are given in Table 2.

The symbols for the test compounds used in Table 2 have the same meanings as those in Example 11.

TABLE 2

| Run No. | Test Compound | Amount Added (pts. by weight) | Degree of Discoloration | |
|---|---|---|---|---|
| | | | After 30 Min. | After 60 Min. |
| Present Invention | | | | |
| 1 | I-1 | 0.5 | Pale Yellow | Yellowish Brown |
| 2 | I-2 | 0.5 | " | Yellowish Brown |
| 3 | I-1/AO-4 | 0.2/0.3 | " | Yellowish Brown |
| 4 | I-1/AO-5 | 0.2/0.3 | " | Yellowish Brown |
| 5 | I-2/AO-4 | 0.2/0.3 | " | Yellowish Brown |
| 6 | I-2/AO-4 | 0.1/0.4 | " | Yellowish Brown |
| 7 | I-2/AO-5 | 0.2/0.3 | " | Yellowish Brown |
| 8 | I-2/AO-5 | 0.1/0.4 | " | Yellowish Brown |
| Comparison | | | | |
| 9 | AO-1 | 0.5 | Yellowish Brown | Deep Brown |
| 10 | AO-2 | 0.5 | Yellowish Brown | " |
| 11 | AO-3 | 0.5 | Yellowish Brown | Brown |
| 12 | AO-1/AO-4 | 0.2/0.3 | Yellowish Brown | Deep Brown |
| 13 | AO-1/AO-5 | 0.2/0.3 | Yellowish Brown | " |
| 14 | AO-2/AO-4 | 0.2/0.3 | Yellowish Brown | " |
| 15 | AO-2/AO-5 | 0.2/0.3 | Yellowish Brown | " |
| 16 | AO-3/AO-4 | 0.2/0.3 | Yellowish Brown | Brown |
| 17 | AO-3/AO-4 | 0.1/0.4 | Yellowish Brown | " |
| 18 | AO-3/AO-5 | 0.2/0.3 | Yellowish Brown | " |
| 19 | AO-3/AO-5 | 0.1/0.4 | Yellowish Brown | " |
| 20 | No Addition | | Dark Brown | Dark Brown |

EXAMPLE 13

Polybutadiene rubber produced by the solution polymerization process and containing no antioxidant (a rubber prepared by extracting a commercially available product, JSR BR-01 with acetone to remove the antioxidant was used) was mixed with each test compound on a roll kneader. The thus obtained rubber was used as a test rubber, and tests on the stability against heat and oxidation and the resistance to heat discoloration were carried out. The stability against heat and oxidation was evaluated in terms of time to when the gel content had reached 10% by weight (designated as Gel I.P.) by subjecting the test rubber to aging by heat in a gear oven at 100° C. and measuring the gel content (i.e., a toluene-insoluble matter) at 15 hours' intervals.

The resistance to heat discoloration was evaluated in terms of color hue of rubber 15 hours, 60 hours and 120 hours after aging by heat in a gear oven at 100° C. The results obtained are given in Table 3.

In Table 3, the symbols AO-6 and AO-7 for the test compounds stand for the compounds given below, and the rest of the symbols have the same meanings as those in Example 16.

AO-6 Tris(nonylphenyl) Phosphite
AO-7 Distearyl Pentaerythritol Diphosphite

TABLE 3

| Test Compound | Present Invention Run No. | | | | | | | | Comparison Run No. | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Phenol Type | | | | | | | | | | | | | |
| I-1 | 1.0 | | 0.25 | 0.25 | | | | | | | | | |
| I-2 | | 1.0 | | | 0.25 | 0.10 | 0.25 | 0.10 | | | | | |
| AO-1 | | | | | | | | | 1.0 | | | | |
| AO-2 | | | | | | | | | | 1.0 | | | |
| AO-3 | | | | | | | | | | | 1.0 | | |
| Sulfur Type | | | | | | | | | | | | | |
| AO-4 | | | 0.75 | | | 0.75 | 0.90 | | | | | 1.0 | |
| AO-5 | | | | 0.75 | | | | 0.75 | 0.90 | | | | 1.0 |
| Phosphorus Type | | | | | | | | | | | | | |
| AO-6 | | | | | | | | | | | | | |
| AO-7 | | | | | | | | | | | | | |
| Gel I.P. (hrs) | 155 | 135 | 160 | 160 | 155 | 150 | 190 | 175 | 80 | 75 | 85 | 20 | 20 |
| Resistance to Heat Discoloration | | | | | | | | | | | | | |
| 0 Hr. | White | White | White | White | White | White | White | White | White | White | White | White | White |
| 15 Hrs. | " | " | " | " | " | " | " | " | " | " | " | Pale Yellow | Pale Yellow |
| 60 Hrs. | " | " | " | " | " | " | " | " | " | " | " | Yellow | Yellow |
| 120 Hrs. | " | " | " | " | " | " | " | " | Pale Yellow | Pale Yellow | Pale Yellow | " | " |

| Test Compound | Comparison Run No. | | | | | | | | | | | | |
|---|---|---|---|---|---|---|---|---|---|---|---|---|---|
| | 14 | 15 | 16 | 17 | 18 | 19 | 20 | 21 | 22 | 23 | 24 | 25 | 26 |
| Phenol Type | | | | | | | | | | | | | |
| I-1 | | | | | | | | | | | | | |
| I-2 | | | | | | | | | | | | | |
| AO-1 | | | 0.25 | 0.25 | 0.25 | 0.25 | | | | | | | |
| AO-2 | | | | | | | 0.25 | 0.25 | 0.25 | 0.25 | | | |
| AO-3 | | | | | | | | | | | 0.25 | 0.10 | 0.25 |
| Sulfur Type | | | | | | | | | | | | | |
| AO-4 | | | 0.75 | | | 0.75 | | | | 0.75 | 0.90 | | |
| AO-5 | | | | 0.75 | | | 0.75 | | | | | | 0.75 |
| Phosphorus Type | | | | | | | | | | | | | |
| AO-6 | 1.0 | | | | 0.75 | | | | 0.75 | | | | |
| AO-7 | | 1.0 | | | | 0.75 | | 0.75 | | 0.75 | | | |
| Gel I.P. (hrs) | 30 | 30 | 60 | 60 | 85 | 70 | 55 | 55 | 75 | 60 | 80 | 75 | 85 |
| Resistance to Heat Discoloration | | | | | | | | | | | | | |
| 0 Hr. | White | White | White | White | White | White | White | White | White | White | White | White | White |
| 15 Hrs. | " | " | " | " | " | " | " | " | " | " | " | " | " |
| 60 Hrs. | Yellow | Yellow | Pale Yellow | Pale Yellow | " | " | Pale Yellow | Pale Yellow | " | Pale Yellow | Pale Yellow | Pale Yellow | Pale Yellow |
| 120 Hrs. | " | " | Yellow | Yellow | Pale Yellow | Yellow | Yellow | Yellow | Yellow | Yellow | Yellow | Yellow | Yellow |

| Test Compound | Comparison Run No. | | | |
|---|---|---|---|---|
| | 27 | 28 | 29 | 30 |
| Phenol Type | | | | |
| I-1 | | | | NO ADDITION |
| I-2 | | | | " |
| AO-1 | | | | " |
| AO-2 | | | | " |
| AO-3 | 0.10 | 0.25 | 0.25 | " |
| Sulfur Type | | | | |
| AO-4 | | | | " |
| AO-5 | 0.90 | | | " |
| Phosphorus Type | | | | |
| AO-6 | | 0.75 | | " |
| AO-7 | | | 0.75 | " |

TABLE 3-continued

| | | | | |
|---|---|---|---|---|
| Gel I.P. (hrs) | 80 | 115 | 115 | 5 |
| Resistance to Heat Discoloration | | | | |
| 0 Hr. | White | White | White | White |
| 15 Hrs. | " | " | " | Yellow |
| 60 Hrs. | Pale Yellow | " | " | " |
| 120 Hrs. | Yellow | Pale Yellow | Pale Yellow | " |

While the invention has been described in detail and with reference to specific embodiments thereof, it will be apparent to one skilled in the art that various changes and modifications can be made therein without departing from the spirit and scope thereof.

What is claimed is:

1. An acetylene carbamide derivative of the general formula (I):

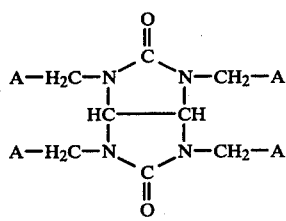

wherein A represents

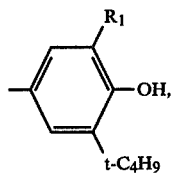

in which $R_1$ represents a hydrogen atom or an alkyl group having 1 to 4 carbon atoms.

2. The acetylene carbamide derivative according to claim 1, wherein the substituent $R_1$ represents a hydrogen atom, a methyl group or a t-butyl group.

3. A process for producing an acetylene carbamide derivative of the general formula (I):

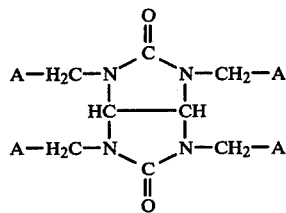

wherein A represents

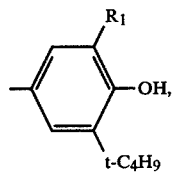

in which $R_1$ represents a hydrogen atom or an alkyl group having 1 to 4 carbon atoms, which comprises reacting acetylene carbamide and a p-hydroxybenzyl alcohol derivative of the general formula (III):

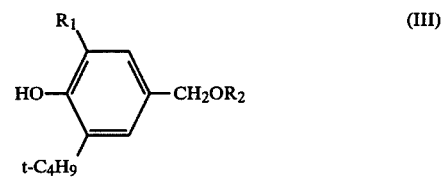

wherein $R_1$ is as defined above, and $R_2$ represents a hydrogen atom or an alkyl group having 1 to 4 carbon atoms, in a solvent in the presence of a catalyst.

4. A process for producing an acetylene carbamide derivative of the general formula (I):

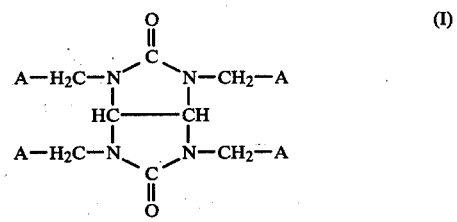

wherein A represents

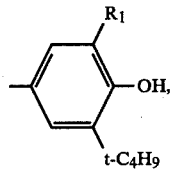

in which $R_1$ represents a hydrogen atom or an alkyl group having 1 to 4 carbon atoms, which comprises reacting acetylene carbamide and a dialkyldithiocarbamate derivative of the general formula (IV):

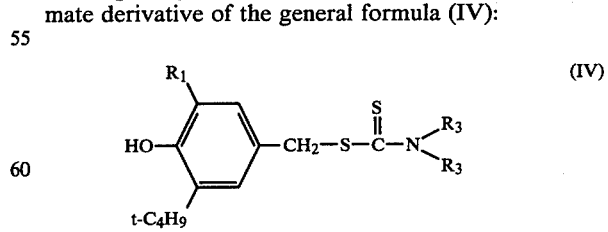

wherein $R_1$ is as defined above, and $R_3$ represents an alkyl group having 1 to 4 carbon atoms, in a solvent in the presence of a catalyst.

5. A process for producing an acetylene carbamide derivative of the general formula (I):

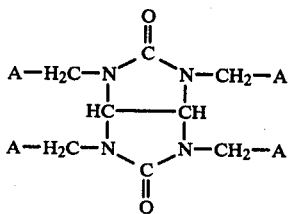

wherein A represents

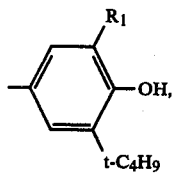

in which R₁ represents a hydrogen atom or an alkyl group having 1 to 4 carbon atoms, which comprises simultaneously reacting acetylene carbamide, formaldehyde and a phenol of the general formula (V):

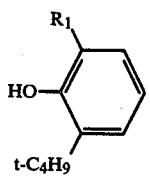

wherein R₁ is an defined above, in a solvent in the presence of a catalyst.

6. The process according to claim 3, 4 or 5, wherein said solvent is a lower alcohol.

7. The process according to claim 3, 4 or 5, wherein said catalyst is a basic catalyst.

8. The process according to claim 7, wherein said catalyst is an alkali metal hydroxide or an alkali metal alkoxide.

9. The process according to claim 3, 4 or 5, wherein the reaction is conducted at a temperature of 20° to 200° C.

10. The process according to claim 9, wherein the reaction is conducted under reflux condition.

11. The process according to claim 3, wherein the molar ratio of acetylene carbamide to the p-hydroxybenzyl alcohol derivative is 1:3.5 to 1:6.

12. The process according to claim 4, wherein the molar ratio of acetylene carbamide to the dialkyldithiocarbamate derivative is 1:3.5 to 1:5.

13. The process according to claim 5, wherein the molar ratio of acetylene carbamide to the phenol to formaldehyde is 1:3.5 to 8:3.5 to 8.

14. A composition comprising an organic substance susceptible to deterioration by light or oxygen and an effective amount to inhibit said deterioration of an acetylene carbamide derivative of the general formula (I):

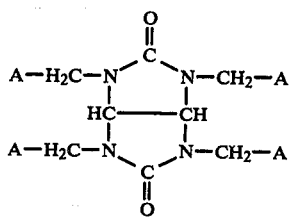

wherein A represents

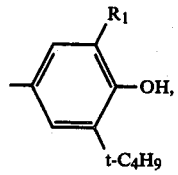

in which R₁ represents a hydrogen atom or an alkyl group having 1 to 4 carbon atoms.

15. The stabilized composition according to claim 14, wherein said organic substance is a polymer.

16. The stabilized composition according to claim 15, wherein said polymer is a synthetic resin, a synthetic rubber or natural rubber.

17. The stabilized composition according to claim 16, wherein said synthetic resin is a polyolefin or an acrylonitrile-butadiene-styrene copolymer.

18. The stabilized composition according to claim 17, wherein said polyolefin is polypropylene.

19. The stabilized composition according to claim 16, wherein said synthetic rubber is butadiene rubber.

20. A stabilizer for organic substances which contains in combination an acetylene carbamide derivative of the general formula (I):

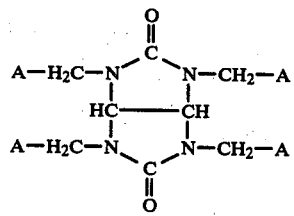

wherein A represents

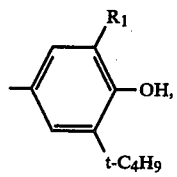

in which R₁ represents a hydrogen atom or an alkyl group having 1 to 4 carbon atoms, and a dialkyl-3,3'-thiodipropionate of the general formula (VI):

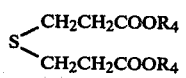

wherein R₄ represents an alkyl group having 12 to 20 carbon atoms or a pentaerythritol-tetrakis(β-alkylthiopropionate) of the general formula (VII):

$$(R_5-S-CH_2CH_2\underset{\underset{O}{\|}}{C}OCH_2)_4C \qquad (VII)$$

wherein R₅ represents an alkyl group having 4 to 20 carbon atoms.

21. The stabilizer for organic substances according to claim 20, wherein the proportion of the acetylene carbamide derivative to the dialkyl-3,3'-thiodipropionate or pentaerythritol-tetrakis(β-alkylthiopropionate) is 1:0.5 to 1:15 by weight.

22. The stabilizer composition of claim 15 in combination with a polymer which is susceptible to deterioration by light or oxygen, the stabilizer being present in an amount effective to inhibit said deterioration.

* * * * *